United States Patent [19]
Cawood

[11] 4,449,971
[45] May 22, 1984

[54] URINE COLLECTION METHOD

[76] Inventor: Charles D. Cawood, 11527 N. Lou Al Ct., Houston, Tex. 77024

[21] Appl. No.: 381,071

[22] Filed: May 24, 1982

[51] Int. Cl.³ ............................................. A61M 31/00
[52] U.S. Cl. ........................................ 604/54; 604/328
[58] Field of Search .................... 604/49, 54, 327–329, 604/332, 345–347, 349, 350, 351, 353, 331; 128/760, 767, 768, DIG. 24

[56] References Cited

U.S. PATENT DOCUMENTS

| | | | |
|---|---|---|---|
| 2,612,895 | 10/1952 | Magee | 604/327 |
| 2,900,979 | 8/1959 | Bishop | 604/327 |
| 3,672,372 | 6/1972 | Heimlich | 604/54 |
| 3,897,785 | 8/1975 | Barto | 604/345 |
| 4,224,610 | 9/1980 | Quinby | 604/332 |
| 4,230,115 | 10/1980 | Walz, Jr. et al. | 604/54 |
| 4,306,976 | 12/1981 | Bazzato | 604/328 |

*Primary Examiner*—C. Fred Rosenbaum
*Assistant Examiner*—J. L. Kruter
*Attorney, Agent, or Firm*—Chas. W. Rummler

[57] ABSTRACT

A method for collecting urine from a catheterized ambulatory patient. A flat urinary drainage bag is worn by the patient over the abdomen with the bag suspended from a waist-encircling belt. A urethral catheter has a proximal end communicating with the upper portion of the bag just below waist level and a distal end retained within the patient's bladder. A valve-equipped drain tube extends downwardly from the lower edge of the bag, the valve being manually operable for periodically draining the contents of the bag. An anti-reflux flap valve is disposed within the bag at the inlet thereof for preventing reverse-flow of fluid from the bag back into the catheter. Although the inlet for the bag is disposed above the distal end of the catheter when the device is worn by an ambulatory patient, intraperitoneal pressure on the bladder resulting from normal body actions nevertheless causes urine to flow from the bladder into the abdominal bag.

2 Claims, 3 Drawing Figures

URINE COLLECTION METHOD

BACKGROUND

A conventional urinary drainage bag as used by an ambulatory catheterized patient is commonly strapped to the leg at or above the knee so that urine will flow into the bag under the influence of gravity. Such an arrangement has a number of disadvantages that may cause inconvenience, discomfort, and even possible serious injury to the wearer. To prevent such a bag from sliding downwardly along the thigh and below the knee, a wearer often finds it necessary to draw the support straps tightly about the leg, thereby inhibiting venous circulation and often irritating and even excoriating the skin of the leg. As such a bag becomes filled with urine, there is an increased tendency for it to slide downwardly despite the tightness of the straps, eventually putting stress on the urethral catheter and causing further discomfort. The tensioning of a catheter under such circumstances may cause irritation to the neck of the bladder (because of the increased pressure caused by the retention balloon at the catheter's distal end) and, in the case of a male patient, may cause prostate irritation. A descended leg bag also becomes more conspicuous, may tend to inhibit walking and other body movements, and, in general, is likely to cause patient distress, embarrassment, and discomfort.

Even more serious problems may develop for a patient (either ambulatory or bedridden) who has a drainage bag hooked at the bedside while resting in bed. Should the patient, in attempting to get out of bed, accidentally step on the catheter tube, the drainage bag, or the elongated drain tube, or unwittingly catch the bag, catheter, or drain tube on some obstruction, he (she) may cause a pulling force to be exerted on the catheter and its inflated balloon, often producing intense pain and, on occasion, rupturing the urethra and causing bleeding, sepsis, and other severe problems.

SUMMARY OF THE INVENTION

An important aspect of this invention lies in recognizing that gravity flow is not essential for the purpose of filling a urine collection bag, and that intraperitoneal pressures exerted upon the bladder of a catheterized ambulatory patient will cause urine to be "pumped" from the bladder to a level as high as 10 centimeters or more above the distal tip of the catheter. The invention includes the further recognition that because of such intraperitoneal pressure, a highly effective urinary drainage system may be provided for an ambulatory patient in which the collection bag is carried by a waistband or belt and is worn over the patient's abdomen instead of along the inside of the leg. Both the catheter and the bag's drain tube may be relatively short, thereby reducing danger to the patient and greatly facilitating use of the appliance. By positioning the bag's drain tube at a central point along the bag's lower edge, a male wearer may conveniently drain the contents of the bag by simply unzipping his pants, extracting the bag's drainage tube, and opening the drain valve. Both male and female patients have the convenience of being able to empty the urinary collection bags by assuming positions customarily taken during voiding by those who have no urinary afflictions or disabilities, unlike wearers of leg bags who must, in order to drain such bags, adjust their clothing to gain access to the drained tubes located at, or even below, knee level.

Briefly, the collection device takes the form of a flat bag dimensioned to be worn by a patient across the abdomen, the bag having front and rear walls of flexible thermoplastic material joined to each other along their top, bottom and side edges. A belt connects to the bag along the top edge thereof, and a valve-equipped drain tube is located along the bottom edge directly in front of the wearer's pelvis. An inlet tube is joined to the upper portion of the bag, and a one-way inlet valve is disposed within the bag to prevent reflux flow of the bag's contents. Exteriorly, the inlet tube is connected to the proximal end of a conventional urethral catheter equipped with an inflatable balloon at its distal end for retention in the urethra. When the bag is worn, the distal tip of the catheter will normally be about 5 to 10 centimeters below the inlet of the bag; however, intraperitoneal pressure on the bladder associated with common body actions such as walking, bending, and breathing result in a pumping effect that directs fluid from the bladder into the bag, and the anti-refluxing valve prevents reverse flow through the catheter.

Other features, advantages, and objects will become apparent from the specification and drawings.

DRAWINGS

DETAILED DESCRIPTION OF PREFERRED EMBODIMENT

Figure 1:
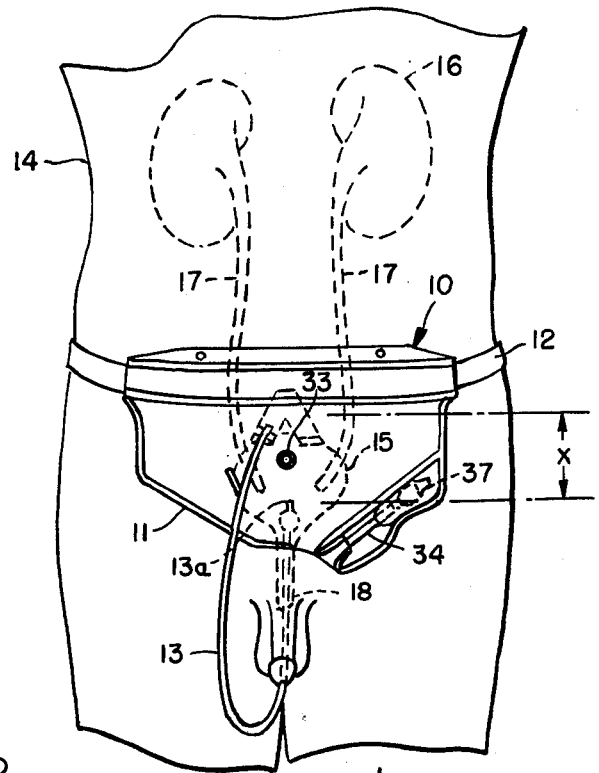
FIG. 1 is a front elevational view of a urine collection device as it would be worn by a catheterized male patient.

Referring to the drawings, the numeral 10 generally designates a urine collection device comprising an abdominal bag 11, a belt 12 for supporting the bag about a patient's waist, and a catheter 13 for conveying urine from the bladder to the collection bag. FIG. 1 illustrates the device as it would be worn by a male patient 14, with catheter 13 extending through the urethra and the distal end 13a of the catheter being disposed within bladder 15. Urine drains into the bladder from kidneys 16 and ureters 17. The urethral sphincter located at 18 would normally control flow from bladder 15; however, the sphincter is rendered inoperative or ineffective by catheter 13, with the result that urine is free to flow from the bladder into the catheter. Catheter 13 is a conventional retention catheter, commonly called a Foley catheter, having an inlet 19 at its distal end 13a. An inflatable balloon 20 is disposed near the tip of the cathether and may be inflated into the expanded condition depicted in broken lines in FIG. 2 to provide retention means for retaining the distal tip of the catheter within the neck of the bladder. A stem 21 providing a suitable self-sealing inflation port is located at the proximal end 13b of the catheter. Inflation and deflation of the balloon is achieved by inserting the needle of a syringe into the inflation port, all as well known in the art.

Bag 11 is flat when empty and is dimensioned to extend over a patient's abdomen or belly as shown in FIG. 1. Specifically, the bag has front and rear panels or walls 11a and 11b, respectively joined together along their top, side, and bottom edges 22–24. Top edge 22 is generally straight and extends horizontally when the bag is worn. Immediately below the top edge is a horizontally-elongated tubular channel 26 defined by parallel heat-seal lines 27, the channel serving as a horizontally-elongated belt loop for receiving belt 12 and thereby supporting or suspending the bag from a patient's waist. Alternatively, belt 12 may be formed integrally with the bag, or may take the form of a pair of straps permanently secured to the bag and projecting laterally therefrom. The construction shown is preferred because bag 11 is a disposable item formed of a suitable thermoplastic material such as, for example, a polyolefin film (e.g., polyethylene) laminated with an appropriate barrier material (e.g., polyvinylidene chloride), whereas the belt would ordinarily be formed of cloth and would be reusable. A belt formed of cotton or any other soft breathable fabric is believed particularly effective, such belt being equipped with a conventional clasp or buckle (not shown) allowing adjustment of the size of the belt so that it extends snugly but comfortably about a wearer's waist.

If desired, the upper edge portion of the bag 11 may be provided with openings 28 that may be used to secure the upper edge of the bag to the patient's undergarments by means of safety pins or other suitable fasteners.

The dimensions of the bag may be varied somewhat depending on the size of the patient. In general, the bag should have a width within the range of about 20 to 40 centimeters (preferably about 30 centimeters) and a height of about 10 to 20 centimeters (preferably about 15 centimeters). In any event, the bag should be dimensioned to extend generally over the wearer's abdomen, from his (her) waist down to the pelvic region, as depicted in FIG. 1. When the bag is so worn, it is positioned at approximately the same height as the wearer's bladder 15.

An inlet tube 29 formed of polyvinyl chloride or other suitable thermoplastic material is heat sealed to the upper front wall 11a of the bag and communicates with the interior of the bag to a suitable one-way valve 30. As shown in the drawings, the exterior portion of the inlet tube is operatively connected to the proximal end 13b of catheter 13. The connection might be a permanent one, although a separable connection is preferred. To facilitate coupling and uncoupling of the catheter and tube and at the same time achieve a secure connection that will not become accidentally disrupted, it has been found desirable to seal a connecting sleeve or nipple 31 to the outer end of the inlet tube, the nipple being stepped as shown (FIG. 2) and being formed of a relatively rigid material such as, for example, polystyrene.

The one-way valve 30 may be formed of a pair of inverted V-shaped flexible thermoplastic strips 30a and 30b heat sealed along their inner and outer edges to define a passage communicating at one end with inlet tube 29 and open at its other end only when fluid pressure within the passage forces the strips 30a and 30b apart at that other end. The anti-refluxing flap valve 30 is centrally positioned within the upper portion of the bag about equal distances from side edges 23 and may be advantageously secured in place by the lower heat seal line 27 that also defines the upper limits of the bag's interior and the lower limits of the belt-receiving channel 26. It will be understood that the same heat seal area that secures inlet tube 29 to the bag, with the inlet tube communicating with the passage of flap valve 30, also seals off the leg of the valve passage immediately adjacent tube 29, with the result that fluid may flow through the valve passage only in the direction indicated generally by arrow 32 in FIG. 2.

To prevent localized bulging of the bag as urine is collected therein, the front and rear walls of the bag may be joined together at a central point or zone by heat seal line 33. Fluid within the bag thereby tends to be distributed more evenly, and audible splashing that might otherwise occur with sudden body movements is eliminated or at least greatly reduced.

Figure 3:
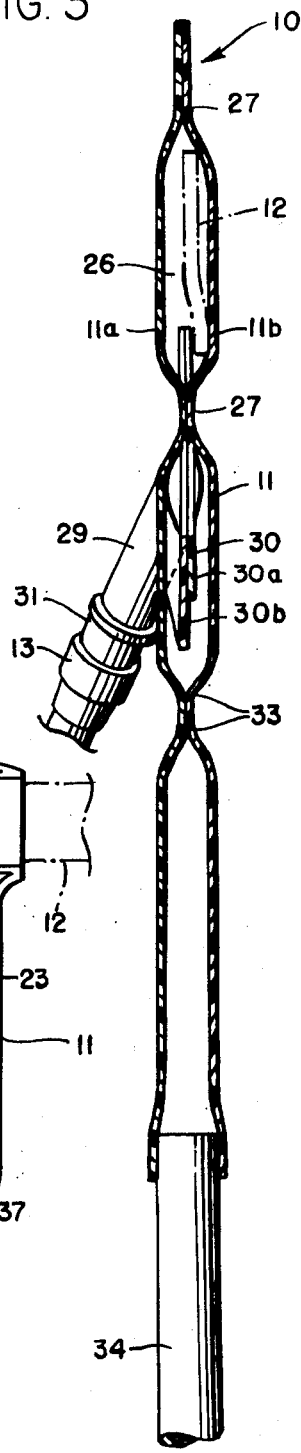
FIG. 3 is a still further enlarged vertical sectional view taken along line 3—3 of FIG. 2.
Figure 2:
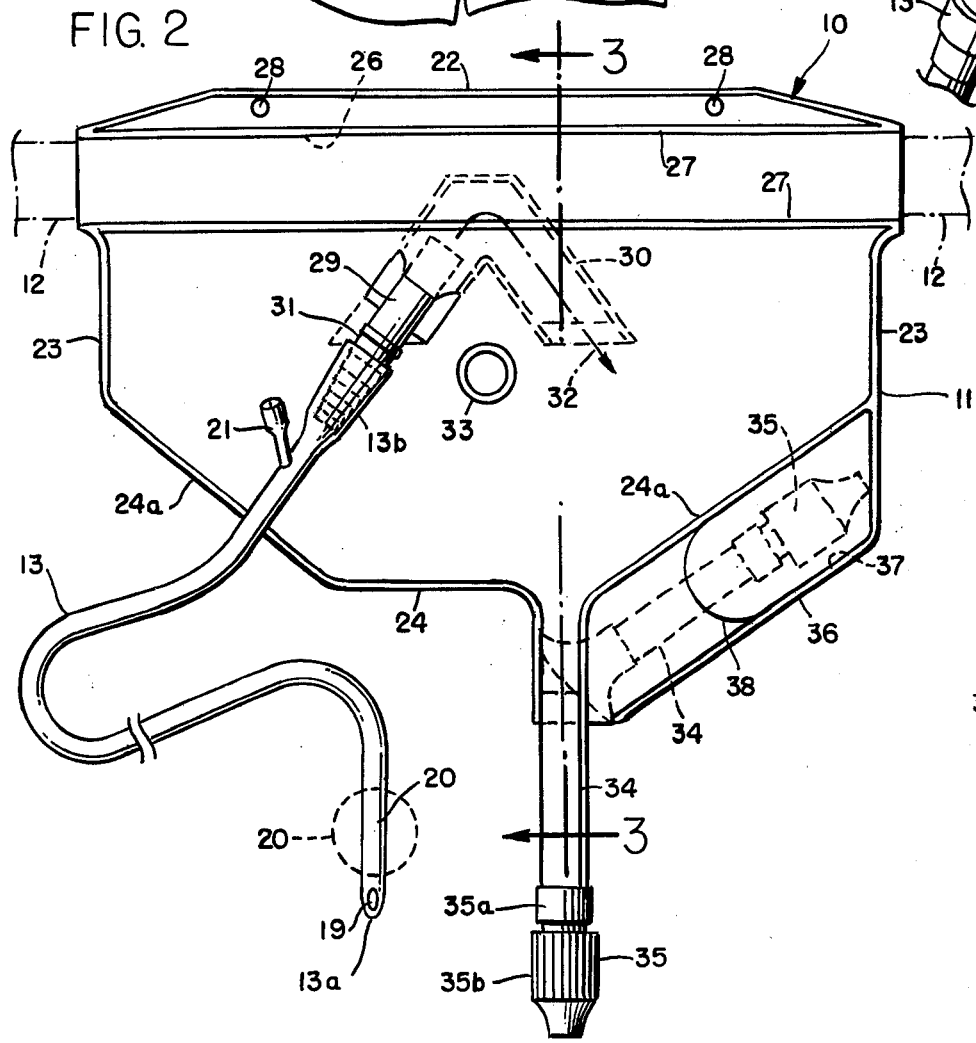
FIG. 2 is an enlarged elevational view of the device.

A short drain tube 34 formed of polyvinyl chloride or other flexible thermoplastic material is heat sealed to the lower edges of the bag and communicates with the bag as most clearly shown in FIGS. 2 and 3. At its free end, the drain tube is equipped with a suitable valve 35. The particular valve depicted in the drawings is composed of two elements 35a and 35b that are threadedly connected to each other. Element 35a is sealed to the lower end of flexible tube 34. Opening and closing of the valve is achieved simply by rotating element 35b one way or the other with respect to element 35a. Since such a valve is entirely conventional and well known for use in collection appliances, a more detailed discussion of its structure and operation is believed unnecessary.

Portions 24a of the bag's lower edge 24 slope downwardly and inwardly to direct fluid towards the centrally-disposed drain tube 34, as indicated in FIG. 2. In the embodiment illustrated, one lower side portion of the bag extends downwardly and is heat sealed along lower edge 36 to define a pocket 37. Slit 38 forms the entrance to that pocket. The drain tube 34 and valve 35 may be inserted within the pocket, as shown in FIG. 1 and in broken lines in FIG. 2, to restrain movement of the drain tube during normal wearing of the bag. When draining of the contents of the bag is desired, the tube is simply removed from the pocket and valve 35 is manipulated into open condition. For reasons already given, such a procedure is far more convenient for the patient than those involved in the draining of a conventional leg bag.

While the urinary collection appliance is shown as it would be worn by a male patient, it is to be understood that the appliance is equally useful for female patients. In both cases, normal body movements or actions, such as breathing, walking, and bending, cause intraperitoneal pressure to be exerted upon the bladder to an extent sufficient to direct urine upwardly through the short length of catheter 13 and into the inlet tube 29 and one-way valve 30 in the upper central portion of the collection bag. Considering inlet tube 29 as a functional extension of the proximal end of catheter 13, it has been found that for an adult patient distance x, which is the vertical distance between the distal tip 13a of the catheter and the point at which tube 29 discharges into the bag, is generally no greater than about 10 centimeters, and usually falls within the range of 5 to 10 centimeters. The intraperitoneal pressures generated as described above may easily exceed 10 centimeters of water. Therefore, despite the fact that the urine collection bag is carried by a belt or waistband 12 over the patient's abdomen, urine from the bladder is readily directed into the bag. Reverse flow, especially as might otherwise occur if the patient were sitting or reclining, is prevented by the anti-refluxing flap valve 30.

While in the foregoing, an embodiment of the invention has been described in considerable detail for purposes of illustration, it will be understood by those skilled in the art that many of these details may be varied without departing from the spirit and scope of the invention.

I claim:

1. A method of collecting urine from an ambulatory patient wearing a urethral catheter having an externally-disposed proximal end and a distal end located within the patient's bladder, and an external urine collection bag communicating with the proximal end of said catheter for collecting urine from the bladder, comprising the steps of locating said bag over the patient's abdomen with the upper portion of said bag disposed at the height of the patient's waist and the lower portion thereof located over the patient's pelvic region, supporting said bag from the patient's waist by means of a belt, and connecting said proximal end of said catheter to said bag for the discharge of urine into the interior thereof at a level slightly above the height of the distal end of said catheter, whereby, intraperitoneal positive pressure exerted on the patient's bladder during normal body activity causes urine to travel from the bladder upwardly through the catheter and into said collection bag, and preventing reverse flow of urine from said bag into said catheter by means of an anti-refluxing valve.

2. The method of claim 1 in which the level at which urine is discharged into the interior of said bag falls within the range of 5 to 10 centimeters above the level of the distal end of said catheter when the patient is standing.

* * * * *